(12) United States Patent
Solingen (10) Patent No.: US 6,809,499 B2
(45) Date of Patent: Oct. 26, 2004

(54) APPARATUS AND METHOD FOR POWERING PORTABLE BATTERY OPERATED LIGHT SOURCES

(75) Inventor: Simon Solingen, Los Angeles, CA (US)

(73) Assignee: Karl Storz GmbH & Co. KG (DE)

( * ) Notice: Subject to any disclaimer, the term of this patent is extended or adjusted under 35 U.S.C. 154(b) by 42 days.

(21) Appl. No.: 10/414,559

(22) Filed: Apr. 10, 2003

(65) Prior Publication Data

US 2003/0193314 A1 Oct. 16, 2003

Related U.S. Application Data

(60) Provisional application No. 60/371,556, filed on Apr. 10, 2002.

(51) Int. Cl.$^7$ .................. H01M 10/44; H01M 10/46
(52) U.S. Cl. ................................. 320/114; 600/178
(58) Field of Search ..................... 320/107, 114, 320/135; 362/20, 572, 574; 600/178, 179, 180, 199, 160

(56) References Cited

U.S. PATENT DOCUMENTS

| | | | |
|---|---|---|---|
| 3,945,371 A | | 3/1976 | Adelman |
| 4,561,430 A | | 12/1985 | Walsh |
| 4,580,198 A | | 4/1986 | Zinnanti, Jr. |
| 4,678,983 A | * | 7/1987 | Rouzies ............... 323/222 |
| 5,130,633 A | | 7/1992 | Maruichi |
| 5,204,608 A | | 4/1993 | Koenck |
| 5,218,284 A | * | 6/1993 | Burns et al. ............ 320/112 |
| 5,323,100 A | | 6/1994 | Iketani |
| 5,434,495 A | | 7/1995 | Toko |
| 5,588,950 A | | 12/1996 | Sano et al. |
| 5,646,503 A | | 7/1997 | Stockstad |
| 5,656,876 A | | 8/1997 | Radley et al. |
| 5,735,794 A | | 4/1998 | Koeda et al. |
| 5,743,848 A | | 4/1998 | Koeda et al. |
| 5,793,187 A | | 8/1998 | DeBauche |
| 5,865,727 A | | 2/1999 | Sano et al. |
| 5,924,978 A | | 7/1999 | Koeda et al. |
| 6,001,058 A | | 12/1999 | Sano et al. |
| 6,004,264 A | | 12/1999 | Sano et al. |
| 6,007,485 A | | 12/1999 | Koeda et al. |
| 6,033,360 A | | 3/2000 | Sano et al. |
| 6,064,185 A | | 5/2000 | Ohno |
| 6,135,947 A | | 10/2000 | Watanabe et al. |
| 6,232,749 B1 | | 5/2001 | Hewes et al. |
| 6,270,454 B1 | | 8/2001 | Sano et al. |
| 6,304,064 B1 | | 10/2001 | Kawai |
| 6,351,100 B1 | | 2/2002 | Altham |
| 6,494,827 B1 | | 12/2002 | Matsumoto et al. |

OTHER PUBLICATIONS

Web pages from Precision Micro Power, Light Bulb Voltage Regulator, Mar. 15, 2002.

* cited by examiner

Primary Examiner—Edward H. Tso
(74) Attorney, Agent, or Firm—St. Onge Steward Johnston & Reens LLC (57) ABSTRACT

A portable imaging system incorporating a portable light source powered by a battery, the output of which is conditioned and regulated to supply an output voltage of a selected level such that the light source provides illuminating light of a selected illumination level and a selected color temperature for use in illuminating the area of interest of an object whose image is observed by means of said portable imaging system.

38 Claims, 7 Drawing Sheets

Figure 1

Prior Art

APPARATUS AND METHOD FOR POWERING PORTABLE BATTERY OPERATED LIGHT SOURCES

PRIORITY DOCUMENT

This application claims the benefit under 35 U.S.C. 119(e) of U.S. Provisional Application No. 60/371,556, filed Apr. 10, 2002.

FIELD OF THE INVENTION

The invention relates to a portable light source system incorporating a power conditioning sub-system, used to supply light for use with medical endoscopes, laryngoscopes, other portable medical illumination devices, and industrial boroscopes.

BACKGROUND OF THE INVENTION

The use of endoscopes has increasingly become important in many fields. For instance, endoscopes are widely used for many medical procedures providing significant advantages such as greatly enhancing a physician's ability to remotely view a body cavity. Not only have endoscopes been widely utilized for surgical procedures, but have also been utilized for assisting a physician to accurately place medical equipment into a body cavity, such as the placing of a laryngoscope in a trachea. Illumination levels and color temperature of the illuminating light is selected and must be maintained in these applications.

For instance, in a surgical procedure, it is absolutely critical that the physician have enough illuminating light in the cavity being operated on to perform the procedure accurately and in a timely manner. If the illumination level is poor, it is challenging for the physician to perform the procedure mistake-free. Additionally, if the illumination level is poor, this will have the effect of slowing the physician in performing the procedure which in turn will increase the length of time the patient will have to be under anesthesia, which is highly undesirable. Therefore, a selected minimum illumination level must be met and must also be maintained throughout the length of the procedure. It should also be noted that illumination levels are very important in applications where, for instance a medical device is being inserted into a body such as a laryngoscope. Without proper illumination, the physician may have difficulty inserting the laryngoscope properly without causing damage to for instance, the vocal cords.

Not only is it important to maintain the proper illumination level in medical applications, but it is also very important to maintain the proper color temperature of the illuminating light. For instance, in many surgical procedures, the physician must first inspect the area or cavity where a potential procedure is to take place and based upon what he observes, identify structures, and determine how to proceed. Being able to accurately differentiate between one type of tissue and the next based upon the color or look and texture is therefore critical to not only diagnosis, but also in performing the procedure mistake-free. Therefore, the color temperature of the illuminating light must be accurately supplied and maintained throughout the procedure.

Endoscopy is also becoming increasingly important for industrial applications. For instance, boroscopes having self contained light sources are utilized to illuminate and image small pipelines, cavities, and internal workings of machinery. Illumination levels and color temperature of the illuminating light must also be maintained for these applications.

For instance, where a boroscope is utilized for inspecting small pipelines, cavities, and internal workings of machinery, in many applications it is important that detailed images be obtained to determine if the equipment has been compromised or if failure is imminent. Failure to detect defects due to poor illumination levels or difficulty in perceiving the color of what is being observed could have catastrophic results. Therefore, maintaining effective illumination levels and accurate color temperature throughout the entire inspection is very important.

Portable, lightweight endoscopy systems for use in both medical and industrial applications are also increasingly being utilized. Traditionally, light sources for portable endoscopes, laryngoscopes, other portable medical illumination devices, and industrial boroscopes have comprised a light source that is powered by a battery source, and some means for connecting or disconnecting the light source to the battery. However, this simple means of providing a portable power source has some inherent problems that greatly limit its use.

Due to the nature of primary or secondary electrochemical power sources (batteries), discharge characteristics are such that their voltage decreases as the total available energy decreases. For some battery types, this is due to an increase in internal impedance, and for others, a combination of the latter and a general drop in open circuit voltage. For some secondary systems, battery age and use history also cause an increase in internal impedance, which in turn will result in unsatisfactory voltage decreases.

In a voltage versus discharge (use) time plot, the slope of the curve depends on the above, as well as the discharge current. Typically, the slope increases with larger currents. When powering a light source, such as is utilized with endoscopes, laryngoscopes, other portable medical illumination devices, and industrial boroscopes, this decrease in voltage causes the intensity of the light source output to decrease exponentially, and to decrease or shift in light color temperature, for instance, a shift towards the red. This is undesirable and in many instances is unacceptable for medical or technical illumination, given that the intensity and color temperature of the illuminating light are critical to the application.

In addition, when primary batteries are used, especially relatively small batteries for added portability and weight reduction, the quantity and quality of light output may become unacceptable due to a drop in circuit voltage, even though the battery may still have a relatively large amount of power remaining. Therefore, the useable lifespan of primary batteries has been greatly reduced when used to power a light source in these critical applications due to unsatisfactory voltage output.

Therefore, what is desired is a portable light source system such as is utilized with endoscopes, laryngoscopes, other medical devices, and industrial boroscopes, that will supply a light output that will not vary in intensity over the life of the battery.

It is also desired to provide a portable light source system, such as is utilized with endoscopes, laryngoscopes, other medical devices, and industrial boroscopes, that will supply a light output that will not shift in color temperature over the life of the battery.

It is further desired to provide a portable light source system, such as is utilized with endoscopes, laryngoscopes, other medical devices, and industrial boroscopes, that will effectively utilize substantially all the energy stored in the battery as practicable for the use while still maintaining strict output requirements.

It is still further desired to provide a portable light source system, such as is utilized with endoscopes, laryngoscopes, other medical devices, and industrial boroscopes, with a minimized size, while still maintaining strict output requirements.

SUMMARY OF THE INVENTION

These objectives are achieved by providing a system configuration in which a light source is connected to the output of a power conditioning circuit, which is in turn, connected to a battery. This configuration provides for a constant voltage level to be delivered to the light source, regardless of variations in battery condition. Providing a constant voltage level to the light source will thereby ensure a constant level of illumination and prevent a shift of the light source color.

The power conditioning circuit will also allow a much larger percentage of the energy stored in the battery to be utilized while still maintaining a determined substantially constant voltage output that will not cause a drop in light intensity or a shift in color. This increase in efficiency will have a positive impact on the "cost of use." The power conditioning circuit may comprise several forms such as, a step-up, step-down, or step-up/down voltage regulator with constant or adaptive output.

The configuration also allows for re-rating of the light source, in this case a tungsten filament bulb, so as to increase efficiency and color temperature of the light source, without causing premature filament burnout. A 10% increase in filament voltage results in approximately a 40% increase in light output, and a desirable higher color temperature, however, it also causes a 70% decrease in filament life. When re-rating a light bulb, this inverse exponential (twelfth power) relationship of filament life to applied voltage requires a tight control of the applied voltage. It is also contemplated that the present invention can further be configured as an adaptive device, to make use of light output feedback to control and stabilize the light source output.

In one advantageous embodiment an apparatus for providing illuminating light of a selected illumination level and color temperature utilized with a portable imaging device is provided comprising a battery, providing electrical power, and a light source. The apparatus further comprises a power conditioning circuit, connecting the battery with the light source and the power conditioning circuit modifies the electrical power based upon a selected threshold parameter representative of a desired illumination level and a desired color temperature of the illuminating light. The apparatus further comprises a portable imaging device, generating an image. Finally the apparatus is provided such that the power conditioning circuit causes the light source to provide illuminating light of an illumination level and a substantially constant color temperature based upon the selected threshold parameter.

In another advantageous embodiment an apparatus for providing illuminating light of a selected illumination level and color temperature utilized with a portable imaging device is provided comprising a battery, providing electrical power, and a light source, having an illumination rating and a color temperature rating. The apparatus also comprises a power conditioning circuit that connects the battery with the light source, and the power conditioning circuit modifies the electrical power to re-rate the light source to, a selected illumination level different from the illumination rating or a selected color temperature different from the color temperature rating.

In still another advantageous embodiment an apparatus for providing illuminating light of a selected illumination level and color temperature utilized with a portable imaging device is provided comprising a battery, providing electrical power, and a light source, having an illumination rating and a color temperature rating. The apparatus also comprises a power conditioning circuit, that connects the battery with the light source, and the power conditioning circuit modifies the electrical power based upon a selected threshold parameter representative of a desired illumination level and a desired color temperature of the illuminating light. The power conditioning circuit also modifies the electrical power to re-rate the light source to, a selected illumination level different from the illumination rating or a selected color temperature different from the color temperature rating. The apparatus further comprises a portable imaging device, generating an image and the power conditioning circuit causes the light source to provide illuminating light of an illumination level and a substantially constant color temperature based upon the selected threshold parameter.

In yet another advantageous embodiment a method is supplied for providing illuminating light of a selected illumination level and color temperature and utilized with a portable imaging device comprising the steps of supplying electrical power with a battery, selecting a light source having an illumination rating and a color temperature rating, and connecting the battery with the light source through a power conditioning circuit. The method further comprises the steps of selecting a threshold parameter representative of a desired illumination level and a desired color temperature of the illuminating light, and modifying the electrical power with the power conditioning circuit based upon the selected threshold parameter. The method further comprises the steps of modifying the electrical power with the power conditioning circuit to re-rate the light source to, a selected illumination level different from the illumination rating or a selected color temperature different from the color temperature rating, and supplying illuminating light of an illumination level and a substantially constant color temperature based upon the selected threshold parameter.

In still another advantageous embodiment a portable endoscopic imaging system is provided comprising a battery, providing electrical power, and a power conditioning circuit, conditioning the electrical power and having a voltage regulator, for maintaining a selected output voltage level. The apparatus further comprises a light source, having a selected illumination level and a selected color temperature, for providing illuminating light of a selected color temperature, and a portable imaging device, for viewing the image of an object illuminated by the illuminating light. In addition, the power conditioning circuit provides a substantially constant output voltage level based upon a selected threshold parameter and said light source provides a substantially constant illumination level and a substantially constant light color temperature based upon a selected threshold parameter.

In yet another advantageous embodiment a portable imaging system comprising a portable power source, a light source, having a selected illumination level and a selected color temperature, and a power conditioning circuit, that provides a constant voltage level based upon a selected threshold parameter. Furthermore, the light source is re-rated to provide a substantially constant illumination level and a substantially constant light color temperature that is higher than the selected illumination level and a color rating that is shifted toward ultra-violet from the selected color temperature.

The invention and its particular features and advantages will become more apparent from the following detailed description considered with reference to the accompanying drawings.

DETAILED DESCRIPTION OF THE DRAWINGS

Figure 1:
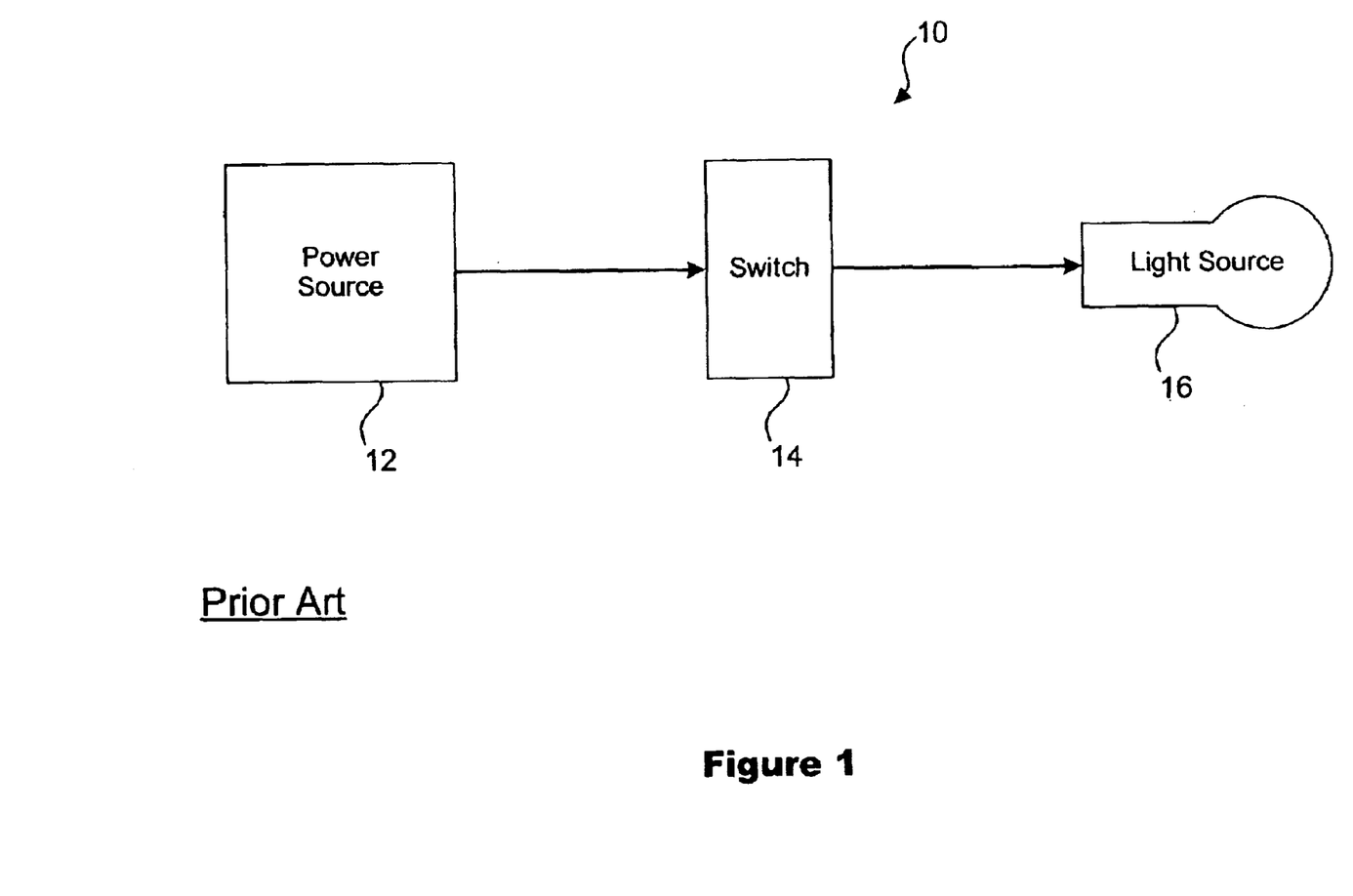
FIG. 1 is a block diagram illustrating the prior art.

A number of various configurations are known in the art for providing a portable light source for various applications. The most basic is illustrated in FIG. 1. In FIG. 1, a portable light source system 10 is illustrated, comprising generally, a power source 12, which may comprise for instance a battery, a switch 14, and a light source 16 for providing illuminating light.

Various types of portable power sources have been utilized including batteries, which have been both rechargeable and non-rechargeable. In addition, various types of light sources have been selected and utilized, which vary based upon the application and desired illumination output.

The switch shown in FIG. 1 has also comprised a number of differing types of switching devices, both manual and automatic. In addition, various devices have been utilized to maximize the amount of energy extracted from power source 12. Specifically, systems have been directed toward stepping up the power output by power source 12 to overcome what has been termed memory problems associated with, for instance, rechargeable nickel-cadmium and nickel-hydrogen batteries. However, in the prior art, the circuit voltage generated for use by light source 16 has not been conditioned and regulated such that a selected illumination level and a selected color temperature of the illuminating light may be maintained based upon a selected parameter, which is highly desirable for medical and industrial applications.

Figure 2:
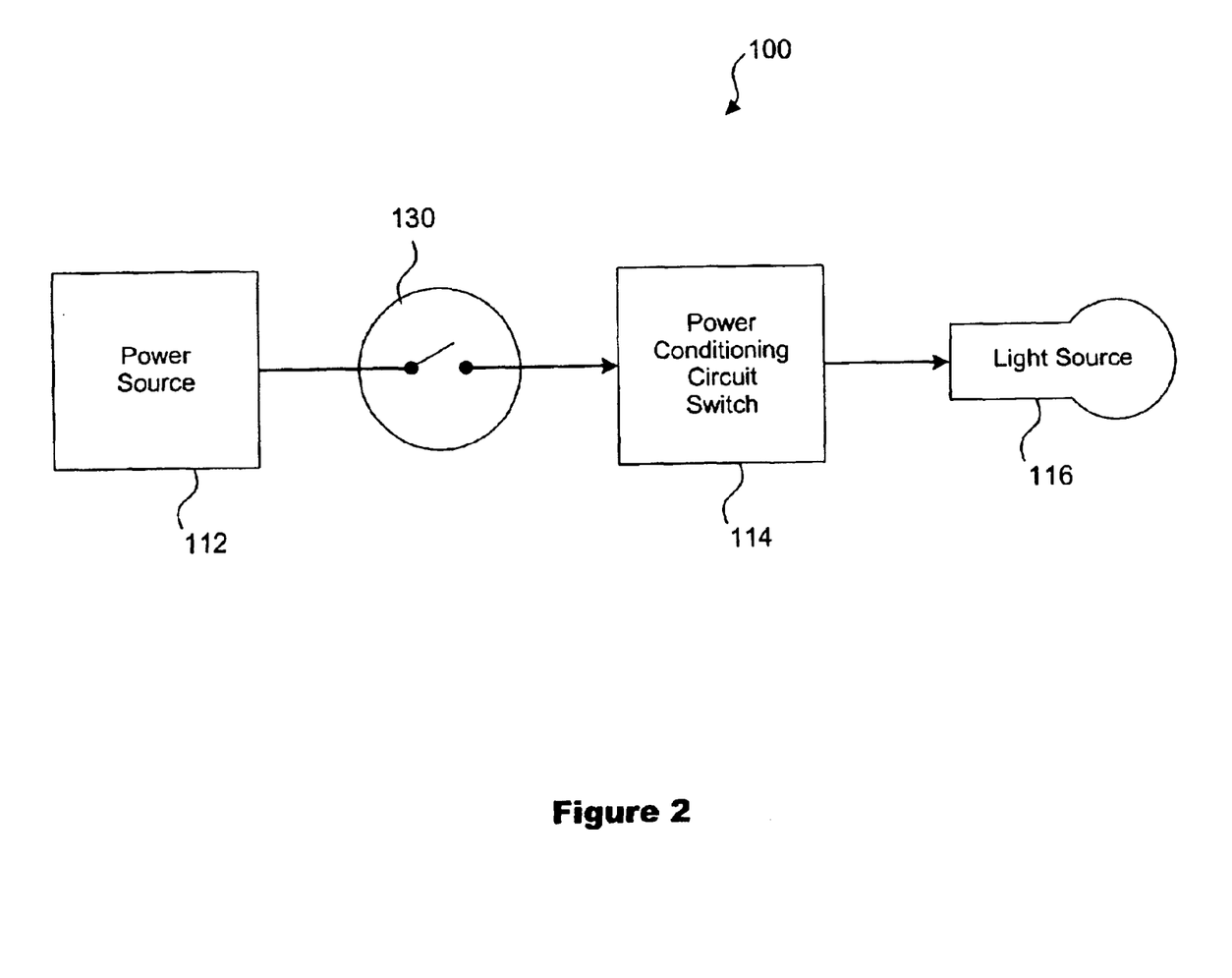
FIG. 2 is a block diagram illustrating an advantageous embodiment of the present invention.

One advantageous embodiment of the present invention is illustrated in FIG. 2. In FIG. 2, a portable light source system 100 is illustrated comprising generally of a power source 112, a power switch 130, a power conditioning circuit 114, and a light source 116.

The power source 112 may comprise any suitable portable power source whether rechargeable or non-rechargeable. In addition, many differing types of batteries may be effectively utilized. In one preferred embodiment, single-cell rechargeable Lithium Ion battery has effectively been utilized as power source 112. Power conditioning circuit 114 will differ, depending upon the chemistry, output voltage, number of cells of the selected battery, and ratings and selected re-rating of the selected light source.

If non-rechargeable batteries are used, it is desirable to utilize as much of the available energy as practicable prior to disposal of the battery. This will operate as a cost saving because the system will utilize as much power as possible from the battery thereby extending the useable life, which will translate into a direct cost saving for the user.

Light source 116 may also comprise any of a number of differing light sources. Depending upon the application, light source 116 will be selected based upon a desired illumination level and/or a desired color temperature. The illumination level of light source 116 is critical to many applications involving medical procedures or industrial applications. It is important that a constant color temperature be maintained over the life of light source 116. Therefore, a light source should be selected that doesn't shift in color as it ages or is used.

In one advantageous embodiment light source 116 comprises a tungsten filament lamp, which is desirable due to its relatively small size, simplicity, and low cost.-Tungsten filament lamps also provide excellent illumination levels and color resolution for their size. For purposes of clarity, in this application, "re-rating" of light sources means the application of a voltage that is higher than the rated voltage listed for the light source. With tungsten filament light sources, the application of a higher voltage will not only increase the illuminating light level, but will also tend to shift the color of the illuminating light toward ultra-violet. Having an increased illuminating light level and shifting the color of the illuminating light towards ultra-violet is highly desirable as it translates into use of a smaller light source and better color resolution. Alternatively, the higher the voltage applied to a light source above the rated voltage, the shorter the life span of the light source. Therefore, benefits and cost savings (smaller size, increased light output and better color resolution, as opposed to shortened light source life) need to be analyzed based upon the application and intended use of the device.

Power conditioning circuit 114 is provided to regulate the voltage level supplied by power source 112 to light source 116. Although various systems have been utilized to maximize the usable power generated by a power source, the power conditioning circuit 114 of FIG. 2 provides regulated power such that, the voltage output of the circuit may be selected based upon various criteria such as the illumination level desired, illumination color requirements, and the life of the tungsten filament light source. Power conditioning circuit 114 may be configured in a number of topologies, for instance but not limited to, fly-back, pulse-width-modulation with transformer coupling, transformerless pulse-frequency-modulation.

Figure 3:
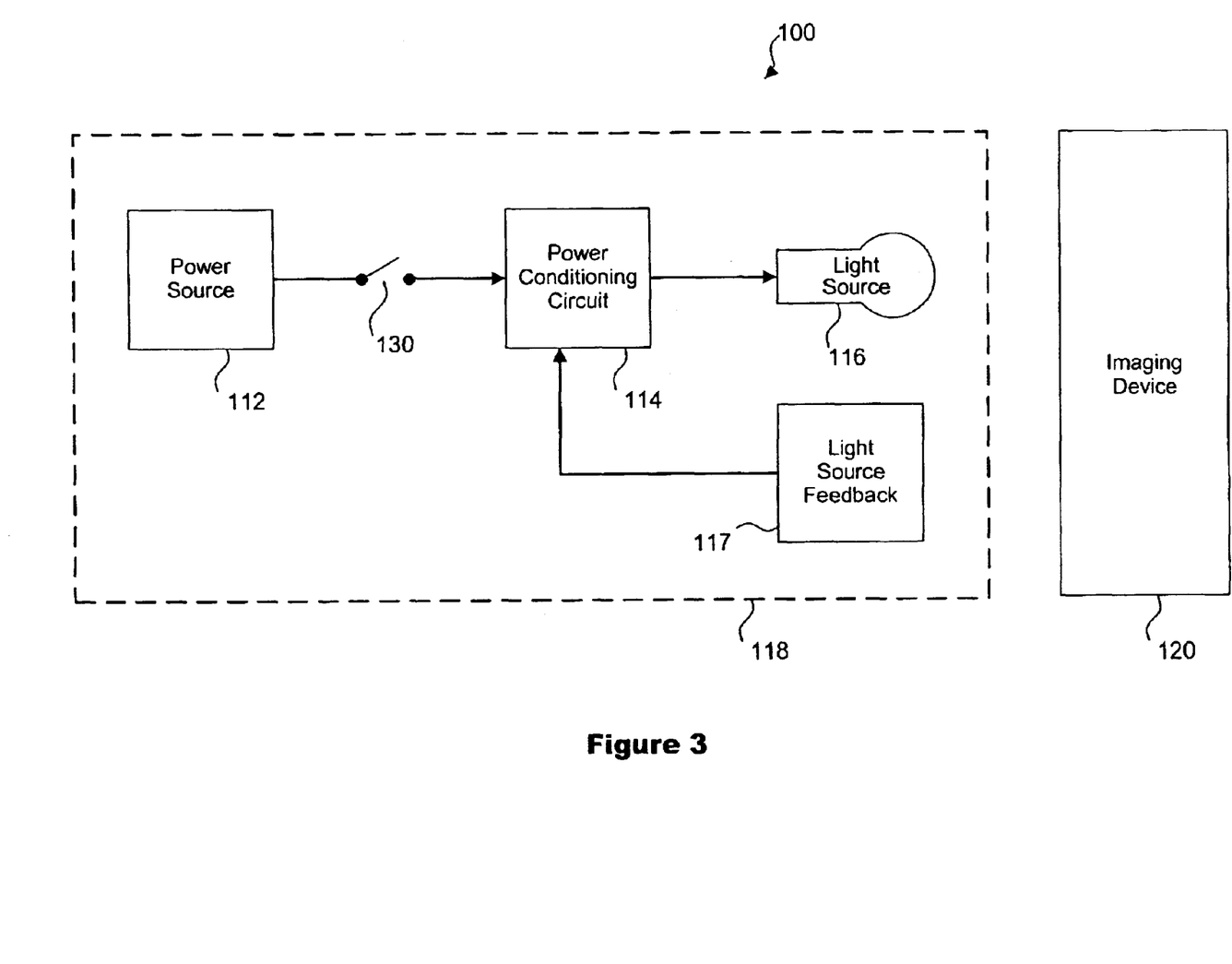
FIG. 3 is a block diagram illustrating another advantageous embodiment of the present invention.

Another advantageous embodiment is illustrated in FIG. 3. Portable light source system 100 is illustrated in FIG. 3 and generally corresponds in functionality, to portable light source system 100 shown in FIG. 2 with a number of additional features. Portable light source system 100 as illustrated in FIG. 3 generally comprises power source 112, power conditioning circuit 114, light source 116, packaging 118, light source feedback 117, and video imaging device 120.

As power source 112, power conditioning circuit 114, and light source 116 generally correspond to their counterparts described in connection with FIG. 2, their functioning will not be re-described here.

Light source feedback 117 is provided to supply illumination feedback information to power conditioning circuit 114. As it is critical in a number of differing applications to provide stable illumination levels and illuminating light having a precise color temperature, light source feedback 117 measures the actual light generated by light source 116 and feeds this information back to power conditioning circuit 114 such that automatic adjustments to the circuit voltage level are made based upon the actual measured light. Light source feedback 117 may comprise any suitable light sensing device for sensing illumination levels and/or illuminating color temperature.

Packaging 118 illustrated in FIG. 3 encloses power source 112, power switch 130, power conditioning circuit 114, and light source 116 in a single, compact, ergonomic, light weight protective container. Packaging 118 may comprise any suitable material, such as but not limited to a polycarbonate, a metal, a metal alloy or any combination thereof.

Also depicted in FIG. 3 is imaging device 120. Imaging device 120 may comprise for instance an endoscope, a laryngoscope, other portable medical devices requiring illumination, or having a light guide to transmit and provide illumination to the area of interest in the object under observation, a boroscope, or any of the above incorporating a portable imaging video system. It is also advantageous if packaging 118 is designed to mate engagingly with imaging device 120 such that easy connection and disconnection of the two may easily be achieved. The connection means may comprise any number of varying mechanical connecting means that will firmly and securely couple the two together such as but is not limited to, friction fitting, mechanical interlocking by protrusions and indentations, rotatable interlocking, bayonet connections, threads, or ball detent connections. It is further conceived that any number of varying locking mechanisms may be effectively utilized to prevent accidental detachment of the two devices.

Imaging device 120 may also have a portable power source (not shown) and a video imaging display (not shown) to display the images picked up by imaging device 120. Many differing endoscopes, laryngoscopes, and boroscopes may be selected depending upon the particular procedure, anatomy of the patient, or the industrial application. It is contemplated then that packaging 118 will vary depending upon the application, so as to effectively mate with a selected imaging device 120.

Figure 4:
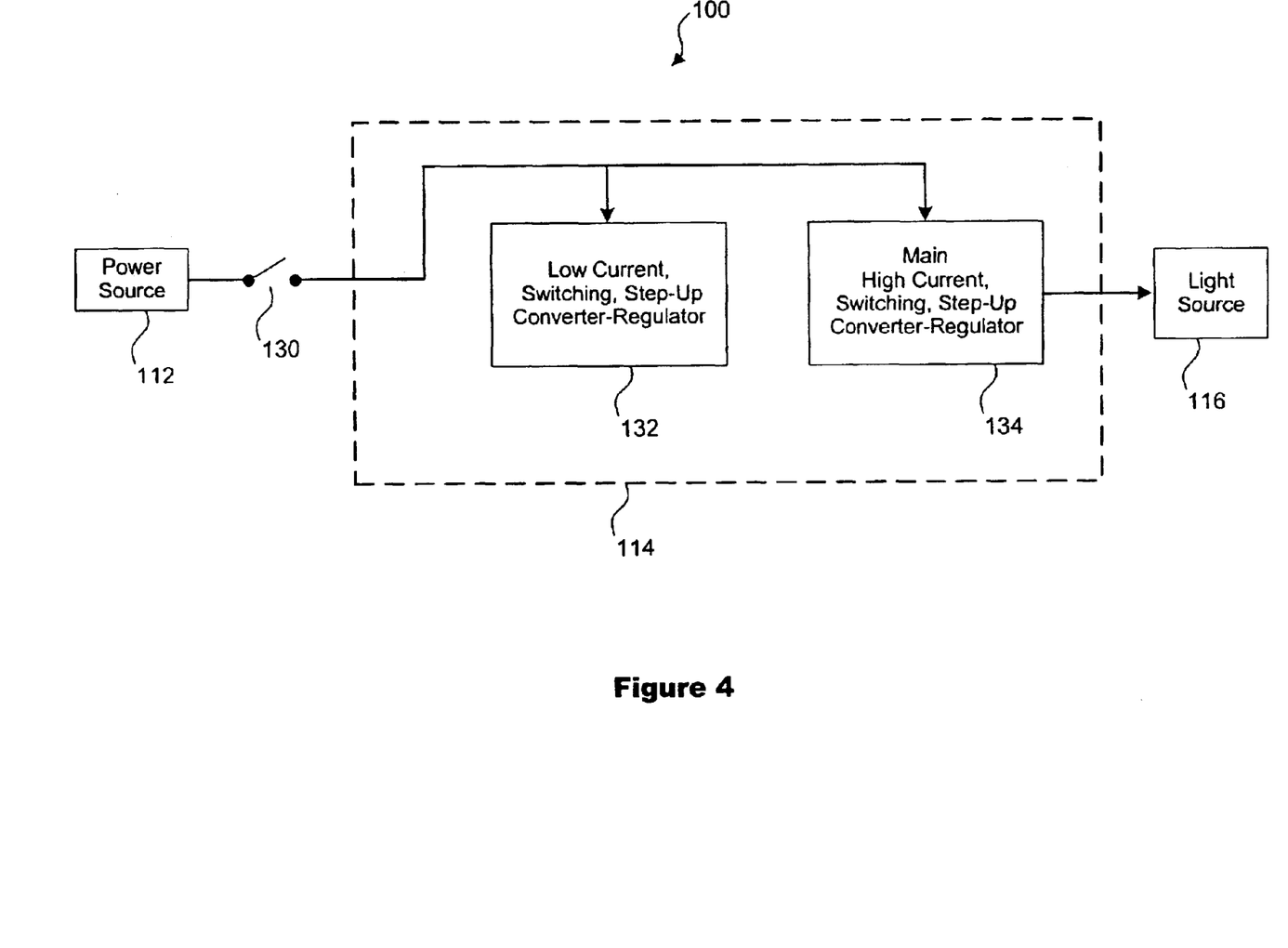
FIG. 4 is a block diagram according to FIG. 2, illustrating still another advantageous embodiment of the present invention.

FIG. 4 is a block diagram illustrating another advantageous embodiment of portable light source system 100. As power source 112 and light source 116 have previously been described in connection with FIG. 2, they will not be described again here. Also shown in FIG. 4 are power switch 130, and a block diagram detail of power conditioning circuit 114. In this embodiment, power conditioning circuit 114 comprises Low Current, Switching, Step-Up Converter-Regulator 132, and Main High Current, Switching, Step-Up Converter-Regulator 134.

Switch 130 may comprise any power disconnecting switch suitable for handling the circuit power. Switch 130 may be a manual or an automatic switch depending upon which is desired.

Main High Current, Switching, Step-Up Converter-Regulator 134 is generally provided to step-up and regulate the output voltage level based upon a selected parameter. Main High Current, Switching, Step-Up Converter-Regulator 134 is connected to switch 130, Low Current, Switching, Step-Up Converter-Regulator 132, and to light source 116. Main High Current, Switching, Step-Up Converter-Regulator 134 utilizes a regulator, which may comprise for instance, an integrated circuit, to convert the electrical power received from power source 112 to the desired output voltage level. For instance, in one example power source 112 may comprise a 3.7 volt single cell rechargeable Lithium Ion battery, light source 116 may comprise a Tungsten Filament lamp rated for 3.7 volts, and the desired output voltage level is selected to be 4.2 volts. In this example, Main High Current, Switching, Step-Up Converter-Regulator 134 converts the 3.7 volts supplied by power source 112 to the desired output voltage level of 4.2 volts and maintains that desired output voltage level. Re-rating of light source 116 in this example will provide approximately 50% more illuminating light than rated and the color of the light will be whiter (shifted towards ultraviolet). The re-rating of light source 116 in this manner will further provide the benefits as previously discussed in connection to FIG. 2.

Low Current, Switching, Step-Up Converter-Regulator 132 is also illustrated in FIG. 4. The sole purpose of Main Low Current, Switching, Step-Up Converter-Regulator 132 is to drive Main High Current, Switching, Step-Up Converter-Regulator 134. When the output voltage supplied to Main High Current, Switching, Step-Up Converter-Regulator 134 is relatively low, the circuit may have difficulty in functioning. To ensure proper functioning with a relatively low battery voltage, Low Current, Switching, Step-Up Converter-Regulator 132 is provided to power Main High Current, Switching, Step-Up Converter-Regulator 134.

Both Low Current, Switching, Step-Up Converter-Regulator 132 and Main High Current, Switching, Step-Up Converter-Regulator 134 may utilize regulators, which in turn, may comprise either integrated circuits or some other appropriate discrete configuration.

Figure 5:
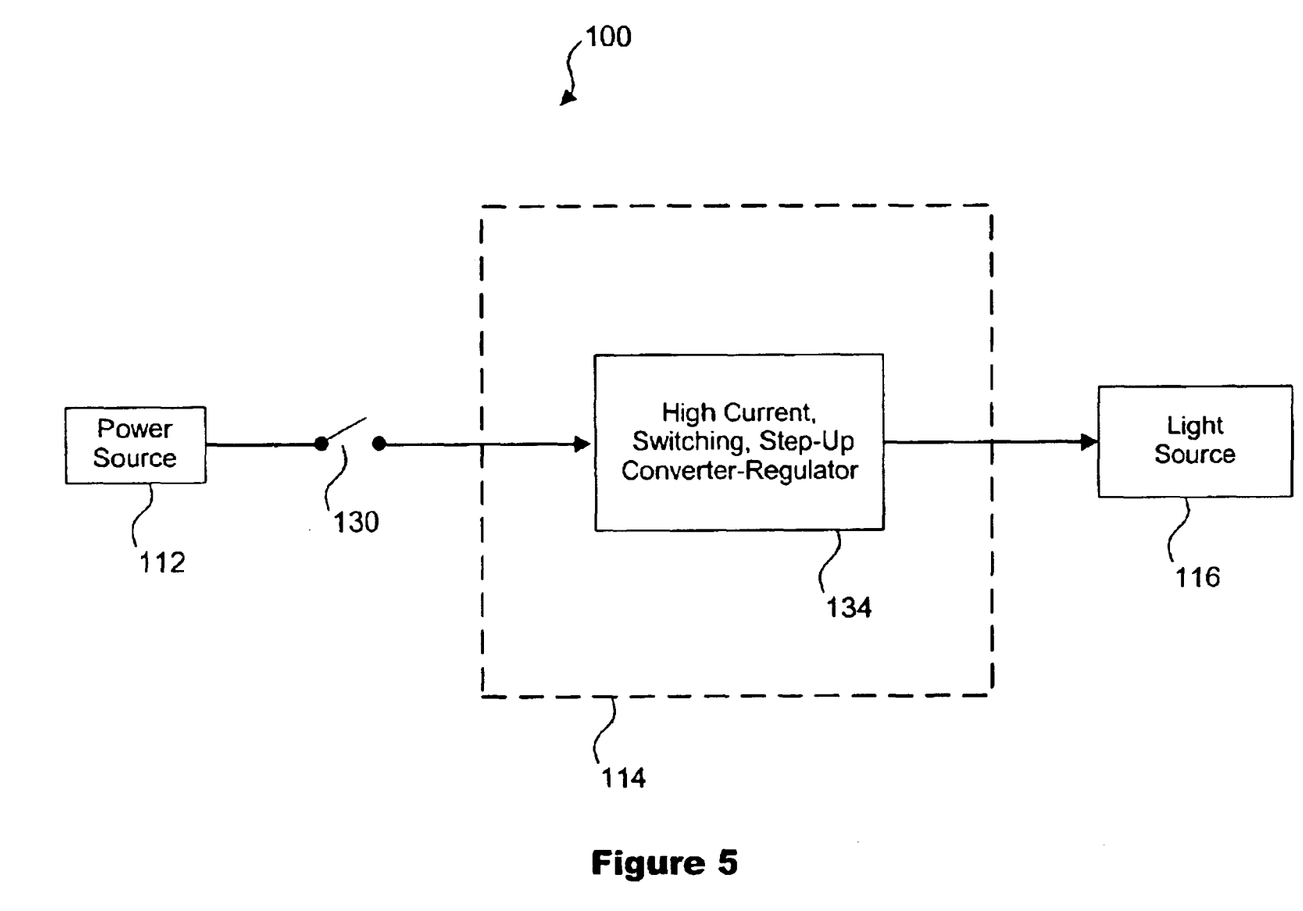
FIG. 5 is a block diagram according to FIG. 2, illustrating yet another advantageous embodiment of the present invention.

FIG. 5 discloses still another advantageous embodiment of the present invention. FIG. 5 comprises a block diagram of portable light source system 100, generally according to FIG. 4, including power source 112, power switch 130, power conditioning circuit 114, and light source 116. Power conditioning circuit 114 is illustrated comprising Main High Current, Switching, Step-Up Converter-Regulator 134. Notably, Low Current, Switching, Step-Up Converter-Regulator 132 is not utilized in this particular embodiment. Where the voltage applied to circuit is high enough such that Main High Current, Switching, Step-Up Converter-Regulator 134 will reliably start up on its own, Low Current, Switching, Step-Up Converter-Regulator 132 is unnecessary. Specifically, in applications where multiple batteries are utilized or the battery supplies a higher voltage, the driving circuit may not be necessary. It should be noted that while portable light source system 100 is simplified in this embodiment, the corresponding size and weight of the entire system may increase with added power capacity. As the remaining elements shown in FIG. 5 have previously been described in connection with FIG. 4, they will not be described here.

Figure 6:
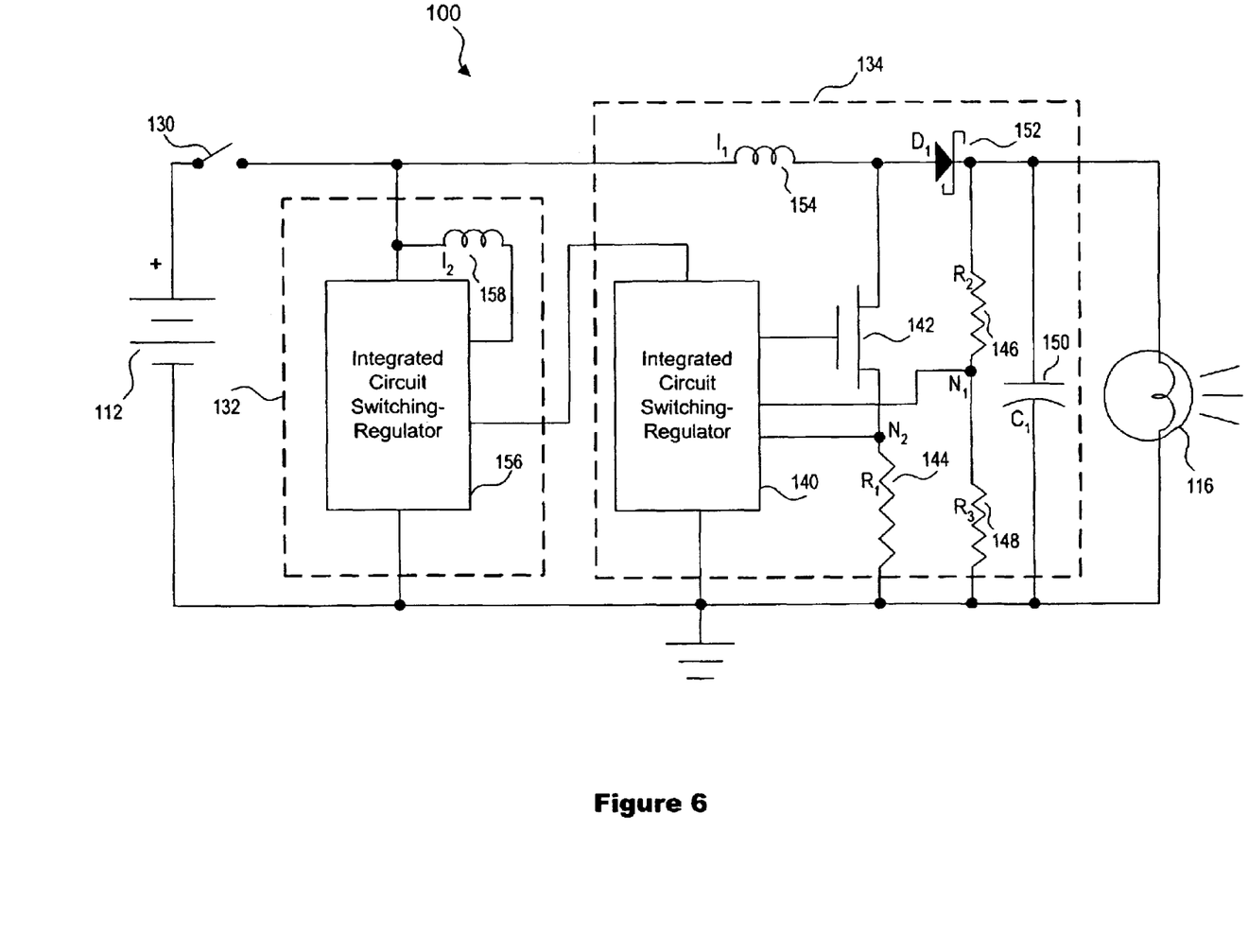
FIG. 6 is a schematic diagram depicting the circuit diagram of the embodiment illustrated in FIG. 4.

FIG. 6 is a schematic diagram of the embodiment according to FIG. 4. Generally, portable light source system 100 as depicted in FIG. 6 comprises a power source 112, in this case a battery, switch 130, Low Current, Switching, Step-Up Converter-Regulator 132, Main High Current, Switching, Step-Up Converter-Regulator 134, and light source 116.

As the functioning and description of power source 112, switch 130, and light source 116 have already been described in connection with FIG. 4, they will not be re-described here.

As illustrated in FIG. 6, Main High Current, Switching, Step-Up Converter-Regulator 134 comprises Integrated Circuit Switching-Regulator 140, transistor 142, resistor $R_1$ 144, resistor $R_2$ 146, resistor $R_3$ 148, capacitor $C_1$ 150, diode $D_1$ 152, and inductor $I_1$ 154.

In this particular embodiment, Integrated Circuit Switching-Regulator 140 is the controller for Main High Current, Switching, Step-Up Converter-Regulator 134, and as illustrated in FIG. 6, comprises an integrated circuit. However, as previously noted, the controller may also comprise any appropriate discrete configuration. Integrated Circuit Switching-Regulator 140 is selected based on the battery voltage, and the power and re-rating requirements of light source 116. Integrated Circuit Switching-Regulator 140 is connected to and is powered by the output of Low Current, Switching, Step-Up Converter-Regulator 132. Integrated Circuit Switching-Regulator 140 in this embodiment has two feedback inputs and one output. At the output, Integrated Circuit Switching-Regulator 140 is connected to the gate of, and controls transistor 142. At a first feedback input, Integrated Circuit Switching-Regulator 140 is connected to a voltage node ($N_1$) created between resistor $R_2$ 146 and resistor $R_3$ 148. At a second feedback input, Integrated Circuit Switching-Regulator 140 is connected to the drain of transistor 142 and one end of resistor $R_1$ 144.

Both resistor $R_2$ 146 and resistor $R_3$ 148 are each selected to have high impedance such that little current will flow through the pair. This voltage divider creates an effective voltage node ($N_1$) to measure circuit voltage across light source 116, which in turn is fed to the first feedback input of Integrated Circuit Switching-Regulator 140. The voltage read at voltage node ($N_1$) will track the voltage across light source 116. Determination of the actual voltage across light source 116 is important as this measurement can be translated to determine and stabilize the illumination level and the color temperature of the illuminating light.

Integrated Circuit Switching-Regulator 140 further comprises a comparator, having an internal reference, such that when the voltage developed at node ($N_1$) is above the internal reference level, then Integrated Circuit Switching-Regulator 140 shuts transistor 142 off. However, when the voltage developed at node ($N_1$) is below the internal reference level, then Integrated Circuit Switching-Regulator 140 begins operating transistor 142 according to a programmed logic sequence based further upon the second input to Integrated Circuit Switching-Regulator 140.

Alternatively, resistor $R_1$ 144 is selected to have very low impedance. Resistor $R_1$ 144 is connected to the source of transistor 142 at one end, and to reference ground at to other end, and further supplies a voltage signal to the second input of Integrated Circuit Switching-Regulator 140. Furthermore, the drain of transistor 142 is connected to inductor $I_1$, which in turn has its other terminal connected to the positive side of power source 112. When transistor 142 is energized, current will begin to flow through resistor $R_1$ 144 such that, based upon the current through resistor $R_1$ 144, a voltage proportional to that current is developed at node ($N_2$), which is fed into Integrated Circuit Switching-Regulator 140. It should be noted that the voltage developed at node ($N_2$) is relatively small as the impedance of resistor $R_1$ 144 is advantageously kept very small.

The output of Integrated Circuit Switching-Regulator 140 controls the switching of transistor 142, which comprises a Field Effect Transistor, such as for instance, a MOSFET. Again it should be noted that, although a MOSFET has effectively been utilized, it is conceived that any Transistor may effectively be utilized. Transistor 142 is operated based upon the programmed logic sequence of Integrated Circuit Switching-Regulator 140, and the first and the second voltage inputs so as to maintain the selected output voltage supplied to light source 116.

Also provided in Main High Current, Switching, Step-Up Converter-Regulator 134 is capacitor $C_1$ 150. Capacitor $C_1$ 150 is connected in parallel across light source 116, having one end connected to reference ground and the other end connected to the active end of inductor 154 through switching rectifier diode 152. Capacitor $C_1$ 150 provides bypassing at the regulated output node to prevent excessive voltage ripple.

The anode of diode $D_1$ 152 is connected to one side of inductor $I_1$ 154 and the cathode of diode $D_1$ 152 is connected to the output capacitor 150.-Diode $D_1$ 152 is provided to prevent current from flowing backwards when transistor 142 is activated, thus, discharging capacitor 150.

Finally, inductor $I_1$ 154 is connected at one end to the positive side of power source 112 and at the other end to the node formed by the anode of diode $D_1$ 152 and the drain of transistor 142. When power is applied to the circuit, transistor 142 is turned on and current flows through inductor $I_1$ 154. When transistor 142 is turned off, the energy stored in inductor $I_1$ 154 discharges through diode $D_1$ 152 to charge capacitor $C_1$ 150, providing the boosted output voltage.

Also illustrated in FIG. 6 is Low Current, Switching, Step-Up Converter-Regulator 132 comprising Integrated Circuit Switching-Regulator 156 and inductor $I_2$ 158. Again, although an integrated circuit is utilized here, any appropriate discrete configuration may effectively be utilized. Inductor $I_2$ 158 operates in the same manner as described for inductor $I_1$ 154. Inductor $I_2$ 158 stores energy for use by Integrated Circuit Switching-Regulator 156 to drive Integrated Circuit Switching-Regulator 140. Integrated Circuit Switching-Regulator 156 is internally supplied with a Field Effect Transistor. Operation is similar to what was described above for converter regulator 134. The output of Integrated Circuit Switching-Regulator 156 is powered by power source 112. In addition, the output of Integrated Circuit Switching-Regulator 156 powers Integrated Circuit Switching-Regulator 140 to ensure reliable start-up under load when the voltage of the power source 112 is too low.

Figure 7:
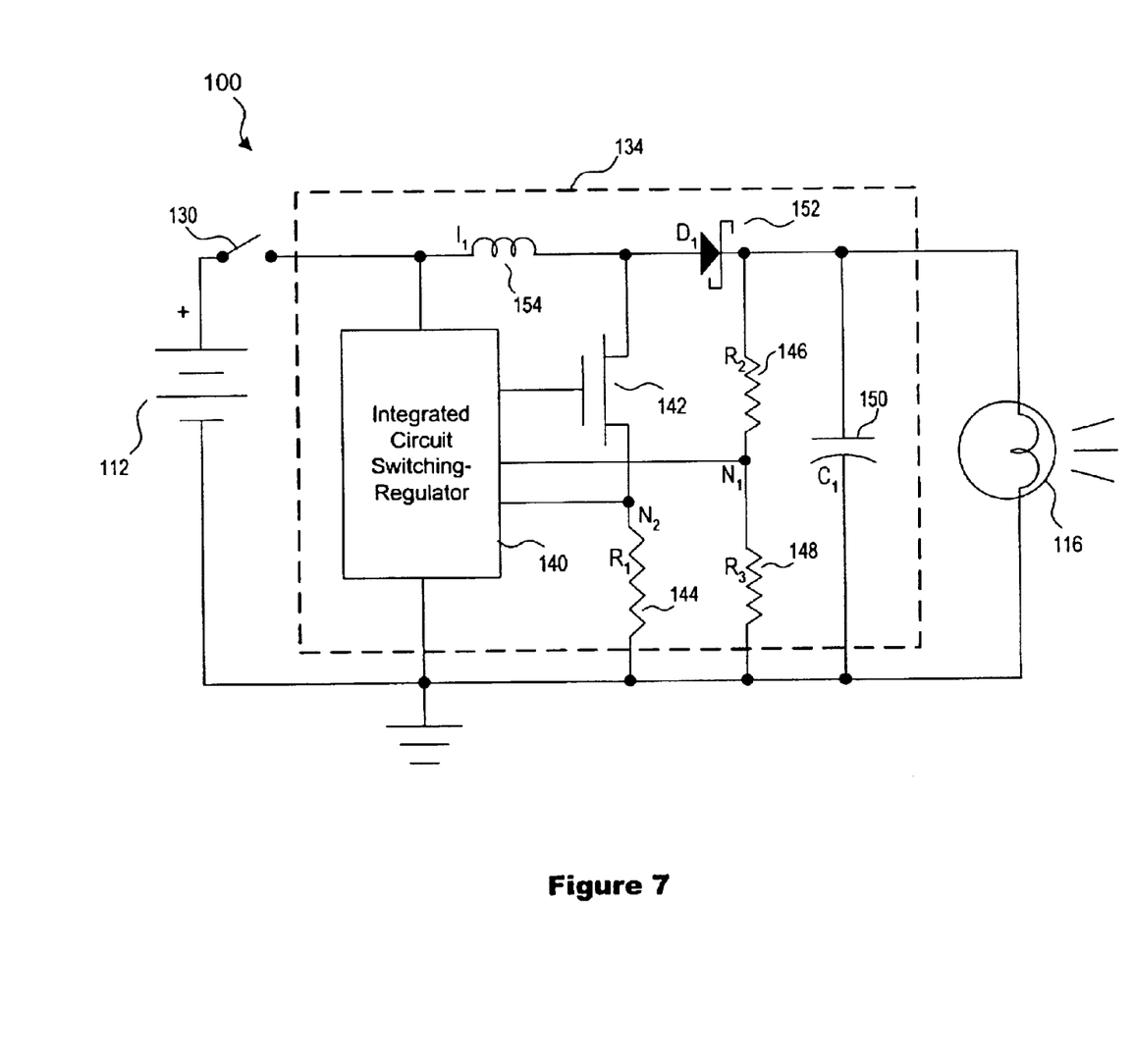
FIG. 7 is a schematic diagram depicting the circuit diagram of the embodiment illustrated in FIG. 5.

FIG. 7 is a schematic diagram of the embodiment according to FIG. 5. Generally, portable light source system 100 as depicted in FIG. 7 comprises a power source 112, in this case a battery, switch 130, Main High Current, Switching, Step-Up Converter-Regulator 134, and light source 116.

As the functioning of these various elements are identical with the corresponding elements as described in FIG. 6, with the exception that Low Current, Switching, Step-Up Converter-Regulator 132 for driving Main High Current, Switching, Step-Up Converter-Regulator 134 is removed because the circuit voltage is high enough to drive the integrated circuit regulator in the Main High Current, Switching, Step-Up Converter-Regulator 134, they will not be re-described.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An apparatus for providing illuminating light of a selected illumination level and color temperature utilized with a portable imaging device comprising;

a battery, providing electrical power;

a light source;

a power conditioning circuit, connecting said battery with said light source, said power conditioning circuit modifying the electrical power based upon a selected threshold parameter representative of a desired illumination level and a desired color temperature of the illuminating light; and a portable imaging device, generating an image;

wherein said power conditioning circuit causes said light source to provide illuminating light of an illumination level and a substantially constant color temperature based upon the selected threshold parameter.

2. The apparatus of claim 1 wherein said portable imaging device is selected from the group consisting of endoscope, laryngoscope, industrial boroscope, video endoscope, video laryngoscope, or industrial video boroscope.

3. The apparatus of claim 1 wherein said light source has an illumination rating and a color temperature rating.

4. The apparatus of claim 3 wherein said power conditioning circuit modifies the electrical power to re-rate the light source to, a selected illumination level different from the illumination rating or a selected color temperature different from the color temperature rating.

5. The apparatus of claim 1 wherein said battery is a rechargeable battery.

6. The apparatus of claim 1 wherein said battery is a non-rechargeable battery.

7. The apparatus of claim 1 wherein said battery is a Lithium Ion battery.

8. The apparatus of claim 1 wherein said power conditioning circuit comprises a switching voltage regulator.

9. The apparatus of claim 1 wherein said light source comprises a tungsten filament lamp.

10. The apparatus of claim 1 wherein said power conditioning circuit further comprises an illumination feedback device, said illumination feedback device measuring the illumination level or the color temperature of the illuminating light.

11. The apparatus of claim 1 further comprising a video camera and display system for viewing the image generated by said portable imaging device.

12. An apparatus for providing illuminating light of a selected illumination level and color temperature utilized with a portable imaging device comprising:

a battery, providing electrical power;

a light source, having an illumination rating and a color temperature rating; and a power conditioning circuit, connecting said battery with said light source, said power conditioning circuit modifying the electrical power to re-rate the light source to, a selected illumination level different from the illumination rating or a selected color temperature different from the color temperature rating.

13. The apparatus of claim 12 further comprising a portable imaging device generating an image.

14. The apparatus of claim 13 wherein said portable imaging device is selected from the group consisting of endoscope, laryngoscope, industrial boroscope, video endoscope, video laryngoscope, or industrial video boroscope.

15. The apparatus of claim 13 further comprising a video camera and display system for viewing the image generated by said portable imaging device.

16. The apparatus of claim 12 wherein said battery is a rechargeable battery.

17. The apparatus of claim 12 wherein said battery is a non-rechargeable battery.

18. The apparatus of claim 12 wherein said battery is a Lithium Ion battery.

19. The apparatus of claim 12 wherein said power conditioning circuit comprises a switching voltage regulator.

20. The apparatus of claim 12 wherein said light source comprises a tungsten filament lamp.

21. The apparatus of claim 12 wherein said power conditioning circuit further comprises an illumination feedback device, said illumination feedback device measuring the illumination level or the color temperature of the illuminating light.

22. An apparatus for providing illuminating light of a selected illumination level and color temperature utilized with a portable imaging device comprising:

a battery, providing electrical power;

a light source, having an illumination rating and a color temperature rating;

a power conditioning circuit, connecting said battery with said light source, said power conditioning circuit modifying the electrical power based upon a selected threshold parameter representative of a desired illumination level and a desired color temperature of the illuminating light, and said power conditioning circuit modifying the electrical power to re-rate the light source to, a selected illumination level different from the illumination rating or a selected color temperature different from the color temperature rating; and a portable imaging device, generating an image;

wherein said power conditioning circuit causes said light source to provide illuminating light of an illumination level and a substantially constant color temperature based upon the selected threshold parameter.

23. The apparatus of claim 22 wherein said portable imaging device is selected from the group consisting of endoscope, laryngoscope, industrial boroscope, video endoscope, video laryngoscope, or industrial video boroscope.

24. The apparatus of claim 22 further comprising a video camera and display system for viewing the image generated by said portable imaging device.

25. The apparatus of claim 22 wherein said power conditioning circuit comprises a switching voltage regulator.

26. The apparatus of claim 22 wherein said power conditioning circuit further comprises an illumination feedback device, said illumination feedback device measuring the illumination level or the color temperature of the illuminating light.

27. A method for providing illuminating light of a selected illumination level and color temperature and utilized with a portable imaging device comprising the steps of:

supplying electrical power with a battery;

selecting a light source having an illumination rating and a color temperature rating;

connecting the battery with the light source through a power conditioning circuit;

selecting a threshold parameter representative of a desired illumination level and a desired color temperature of the illuminating light;

modifying the electrical power with the power conditioning circuit based upon the selected threshold parameter;

modifying the electrical power with the power conditioning circuit to re-rate the light source to, a selected illumination level different from the illumination rating or a selected color temperature different from the color temperature rating;

supplying illuminating light of an illumination level and a substantially constant color temperature based upon the selected threshold parameter.

28. The method according to claim 27 further comprising the step of generating an image with a portable imaging device.

29. The method according to claim 28 wherein the portable imaging device is selected from the group consisting of endoscope, laryngoscope, industrial boroscope, video endoscope, video laryngoscope, or industrial video boroscope.

30. The method according to claim 28 further comprising the step of viewing the image generated by said portable imaging device with a video camera and display system.

31. The method according to claim 27 wherein the battery is a rechargeable battery.

32. The method according to claim 27 wherein the battery is a non-rechargeable battery.

33. The method according to claim 27 wherein the battery is a Lithium Ion battery.

34. The method according to claim 27 wherein the power conditioning circuit comprises a switching voltage regulator.

35. The method according to claim 27 wherein the light source is a tungsten filament lamp.

36. The method according to claim 27 further comprising the step of measuring the illumination level or the color temperature of the illuminating light with an illumination feedback device.

37. A portable endoscopic imaging system comprising:

a battery, providing electrical power;

a power conditioning circuit, conditioning the electrical power and having a voltage regulator, for maintaining a selected output voltage level;

a light source, having a selected illumination level and a selected color temperature, for providing illuminating light of a selected color temperature; and a portable imaging device, for viewing the image of an object illuminated by the illuminating light;

wherein said power conditioning circuit provides a substantially constant output voltage level based upon a selected threshold parameter and said light source provides a substantially constant illumination level and a substantially constant light color temperature based upon a selected threshold parameter.

38. A portable illumination system comprising:

a portable power source;

a light source, having a selected illumination level and a selected color temperature;

a power conditioning circuit, that provides a constant voltage level based upon a selected threshold parameter;

wherein said light source is re-rated to provide a substantially constant illumination level and a substantially constant light color temperature that is higher than the selected illumination level and a color rating that is shifted toward ultra-violet from the selected color temperature.

* * * * *